United States Patent [19]

Fry et al.

[11] 4,401,116
[45] Aug. 30, 1983

[54] GAS FLOW RATE CONTROL DEVICE FOR MEDICAL VENTILATOR

[75] Inventors: Stanley E. Fry; Claude C. Hurd, both of Riverside, Calif.

[73] Assignee: Bear Medical Systems, Inc., Riverside, Calif.

[21] Appl. No.: 212,893

[22] Filed: Dec. 4, 1980

[51] Int. Cl.³ .......................................... A61M 16/00
[52] U.S. Cl. ........................... 128/205.24; 128/204.18
[58] Field of Search ..................... 128/204.25, 205.24, 128/204.21, 204.23, 204.18, 203.14

[56] References Cited

U.S. PATENT DOCUMENTS

| | | | |
|---|---|---|---|
| 2,608,209 | 8/1952 | Bryant | 137/501 |
| 2,879,783 | 3/1959 | Taplin | 137/116.3 |
| 2,917,069 | 12/1959 | Lundy et al. | 137/240 |
| 2,936,152 | 5/1960 | Renick | 251/205 |
| 2,951,501 | 9/1960 | Thylefors | 137/501 |
| 3,083,707 | 4/1963 | Seeler | 128/29 |
| 3,100,620 | 8/1963 | Kates | 251/208 |
| 3,251,359 | 5/1966 | Ismach | 128/29 |
| 3,307,542 | 3/1967 | Andreasen | 128/145.8 |
| 3,351,086 | 11/1967 | Baker | 137/501 |
| 3,554,221 | 1/1971 | McMurry et al. | 137/401 |
| 3,756,229 | 9/1973 | Ollivier | 128/145.8 |
| 4,141,354 | 2/1979 | Ismach | 128/145.6 |
| 4,177,830 | 12/1979 | Munson | 137/401 |
| 4,206,754 | 6/1980 | Cox et al. | 128/204.23 |

Primary Examiner—Henry J. Recla

Attorney, Agent, or Firm—Howard J. Klein

[57] ABSTRACT

A gas flow rate control device for a medical ventilator includes a variable-orifice valve for adjustment of the peak flow rate, and a waveform regulator which supplies controlled gas pressure to the orifice. The regulator maintains a fixed pressure differential between the upstream side of the orifice and a reference pressure. The reference pressure is variable between atmospheric pressure and a pressure which is essentially patient airway proximal pressure. When the reference pressure is patient airway proximal pressure, a constant pressure differential is maintained across the orifice so that a uniform flow rate is maintained. When the reference pressure is atmospheric pressure, a constant pressure is supplied to the upstream side of the orifice, so that the flow rate from the orifice decreases as patient airway proximal pressure on the downstream side of the orifice increases. In one embodiment, the invention uses a pneumatic switch to supply, as the reference pressure, either airway proximal pressure, whereby a uniform flow rate or "square wave" is obtained, or atmospheric pressure, whereby a fixed flow rate deceleration or "taper wave" is obtained for any given peak flow rate setting of the variable orifice. In another embodiment, a valve is used to vary the reference pressure between atmospheric pressure and airway proximal pressure to obtain adjustable values of flow rate deceleration for any given setting of the peak flow orifice.

9 Claims, 6 Drawing Figures

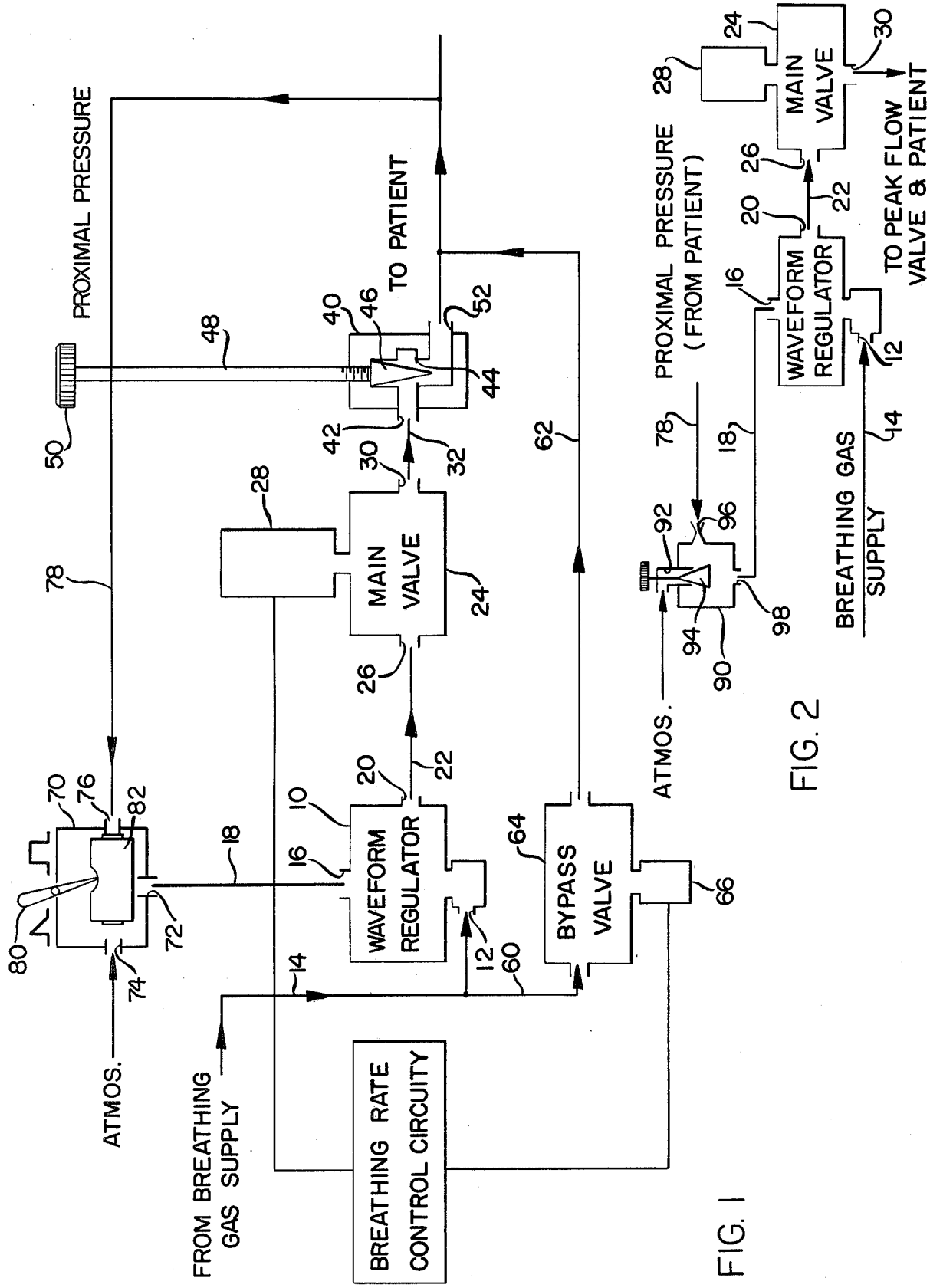

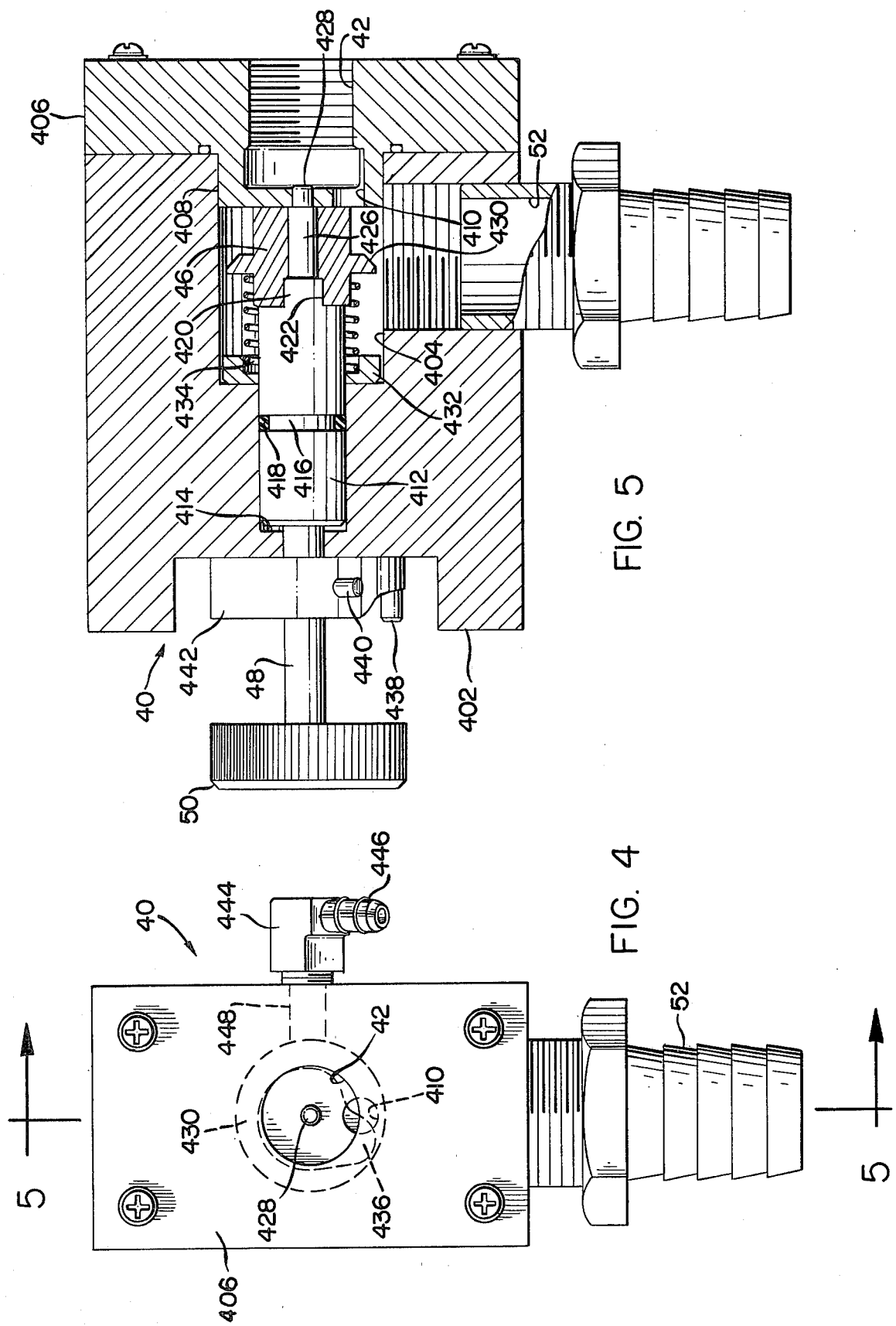

4,401,116

GAS FLOW RATE CONTROL DEVICE FOR MEDICAL VENTILATOR

BACKGROUND OF THE INVENTION

This invention relates to pneumatic controls, and more particularly its relates to a device for controlling the rate of flow of breathing gas supplied to a patient by a medical lung ventilator.

It is of great importance in respiratory therapy carefully to control the gas flows to the patient to avoid injury and to insure that a maximum therapeutic effect is achieved. To this end, various flow control valves are normally installed in the conduit system which connects the ventilator air supply with the patient. One of these valves is typically a peak flow control valve which restricts the maximum volumetric rate of flow of gas to the patient to a predetermined amount for optimal therapeutic effect. The peak flow rate is normally reached during an early stage of inspiration, following by a gradually decreasing intake of air, until the patient is ready to exhale. Another valve is frequently employed to control the rate in which the inspiratory air flow tapers off, with the optimum decay rate, or deceleration, depending upon the type of therapy administered.

Various devices have been employed in the medical ventilator art to provide a controlled airflow decay rate or "taper" rate. Examples of such devices are disclosed in U.S. Pat. No. 3,756,229 to Ollivier and U.S. Pat. No. 4,177,830 to Munson.

Many practitioners in the field of respiratory therapy deem it advisable, with certain patients, to provide the patient with a substantially constant flow rate throughout the inspiratory part of the respiratory cycle. Accordingly, such practitioners require a ventilator which is capable of delivering what is known as a "square wave" airflow, in which the flow rate is maintained at or near the peak flow rate for all or part of the inspiratory period. Accordingly, the ventilator art has sought the development of ventilator devices having both square wave and taper wave capabilities. One approach to this problem is disclosed in the aforementioned patent to Munson. The Munson patent discloses a valve assembly which allows the decay rate to be adjusted without adjusting the initial peak flow rate. The decay rate, or taper, can be adjusted to select a minimum value thereof so as to approximate a square wave type of flow. However, at high peak flow rates, even this minimal amount of taper can be substantial. For example, at peak flow rates of 100 liters per minute (LPM), the "square wave" setting of the valve still allows approximately a 20% taper or decay in the rate of flow.

From the foregoing, it will be appreciated that a medical ventilator which is capable of providing close to true square wave performance, as well as a controllable tapered flow, would be a significant improvement over the prior art.

SUMMARY OF THE INVENTION

The present invention meets the shortcomings of the prior art by providing a device which is capable of achieving very close to true square wave performance while also allowing selectable tapered flow performance.

The invention incorporates a peak flow adjustment valve containing a cammed orifice for selecting an initial peak flow rate. Between the peak flow valve and the breathing gas supply is a pressure regulating device which controls the pressure at the inlet to the peak flow control valve. This pressure regulating device, which functions as what may be called a "wave form regulator", maintains the peak flow control valve inlet pressure at a predetermined pressure differential above a reference pressure. This reference pressure may be varied between atmospheric pressure and a pressure which is essentially equivalent to the patient's airway proximal pressure by means of either a toggle valve (a "pneumatic switch") or a variable orifice valve, e.g., a needle valve. When the reference pressure for the waveform regulator is set to atmospheric pressure, a constant pressure is administered to the peak flow valve inlet. The outlet of the peak flow control valve, being in communication with the air passages of the patient, experiences an increase in pressure as the airway proximal pressure of the patient increases during inhalation. The result is a decreasing pressure differential across the peak flow control valve, so that the flow rate through the valve gradually diminishes, thereby producing a tapered flow rate. However, when the airway proximal pressure is selected as the reference pressure for the wave form regulator, the pressure at the peak flow control valve inlet will be increased in proportion to the increase in patient proximal pressure, since, as previously noted, the wave form regulator is designed to produce a constant pressure differential above the reference pressure. Thus, the pressure differential across the peak flow control valve remains substantially constant with increasing airwave proximal pressure, so that the flow rate through said valve also remains substantially constant for any given peak flow rate setting. The result is substantially true square wave performance.

In the embodiment where a pneumatic switch is used to select the reference pressure, the device is switchable between square wave performance and a fixed degree of flow rate decay, or taper, for any peak flow rate setting of the peak flow control valve. Where means such as a needle valve is employed for reference pressure selection, the reference pressure can be adjusted continuously between atmospheric pressure and airway proximal pressure. Thus, the peak flow control valve inlet pressure can be adjusted to remain constant with increasing airway proximal pressure, to increase at the same rate as the increase in airway proximal pressure, or to increase at a slower rate than the increase in airway proximal pressure, thereby achieving, respectively, maximum tapered flow ("full taper"), square wave, and varying degrees of "partial taper".

Proper timing of the inspiratory flow is provided by a solenoid-actuated valve, which starts and stops the flow from the peak flow control valve in accordance with signals received from the breathing rate control circuitry of the ventilator. A bypass system may advantageously be employed, whereby the wave form regulator peak flow control valve and solenoid actuated valve are bypassed so as to provide the patient with a selected minimum flow rate regardless of the action of the peak flow and waveform regulation apparatus. The bypass circuit may be conveniently opened and closed by a solenoid controlled valve, which is actuated by signals from the breathing rate circuitry.

Thus, it can be seen that the present invention provides the capability of nearly true square wave performance along with selectable degrees of flow rate decay or taper. In addition, the invention allows the selection of different peak flow rates, with the selected peak flow rate being substantially unaffected by the amount of taper selected. Thus, it will be appreciated that the present invention provides the respiratory therapy practitioner with a heretofore unrealized degree of control and flexibility in meeting the highly individualized demands of various patients.

BRIEF DESCRIPTION OF THE DRAWINGS

FIG. 1 is a schematic diagram of peak flow and waveform apparatus, in accordance with the present invention;

FIG. 2 is a partial schematic view of an alternative embodiment of the invention;

FIG. 4 is an elevational view of the inlet side of the peak flow control valve used in the present invention;

FIG. 5 is a sectional view taken along line 5—5 of FIG. 4; and

DETAILED DESCRIPTION OF THE INVENTION

Figure 3:
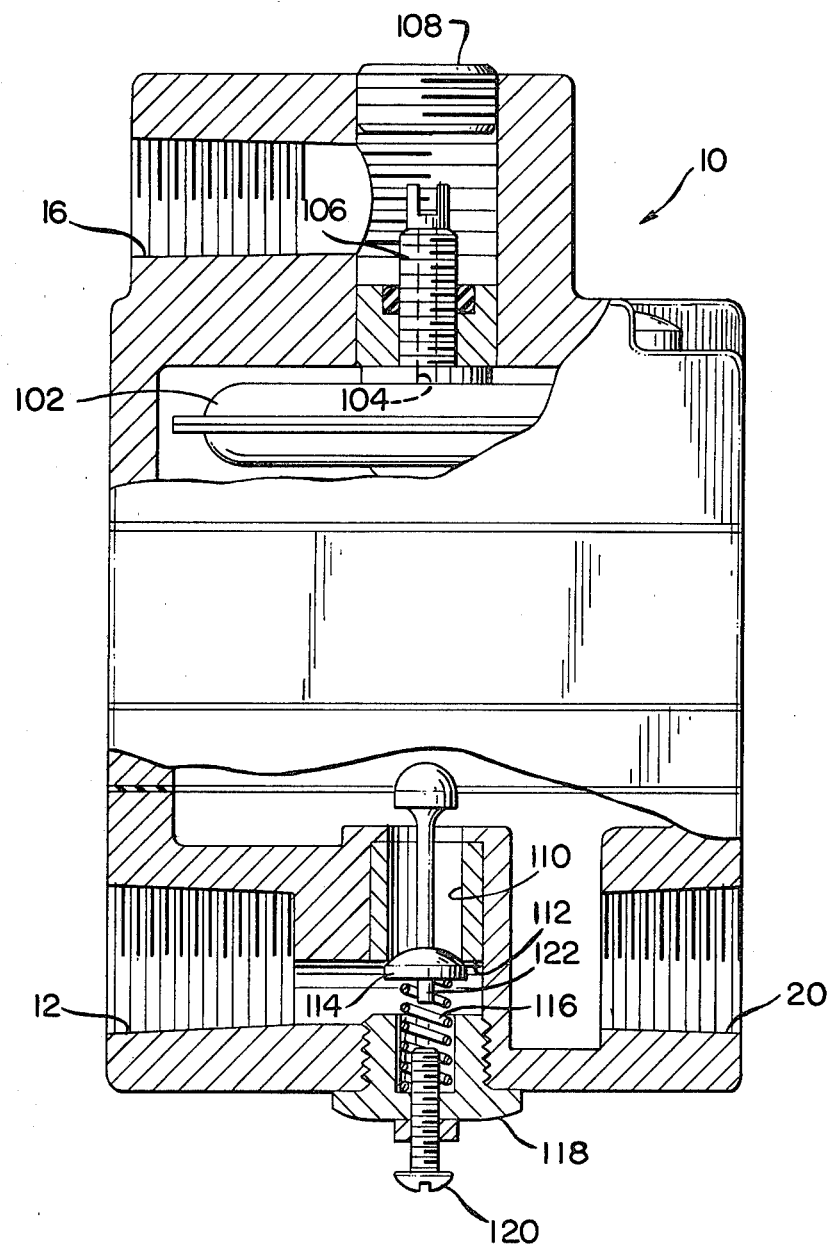
FIG. 3 is an elevational view, partially in section, of the waveform regulator device used in the present invention.

FIG. 1 presents schematically a functional representation of the invention. Essential to the invention is a waveform regulator 10, which is a pressure-regulating device, preferably of the type disclosed in U.S. Pat. No. 2,879,783 to Taplin (the disclosure of which is incorporated herein by reference) with certain modifications, which will be described hereinafter. The waveform regulator 10 has an inlet 12 which receives breathing gas (typically a mixture of air and pure oxygen) from a breathing gas supply line 14. The waveform regulator 10 has a sensing port 16 which receives a reference pressure from line 18, and an outlet port 20, which conducts breathing gas, at a regulated pressure via line 22, to a main valve 24 through a main valve inlet 26. The main valve 24 is a high flow rate, low pressure drop design and is opened by means of a solenoid 28, which, in turn, is energized by a signal from the conventional breathing rate control circuitry of the ventilator. When the main valve 24 is opened, gas flows through the main valve out an outlet 30, through line 32, and into a peak flow control valve 40 via an inlet 42. The peak flow control valve 40 contains a variable orifice 44, the size of which is controlled by a cam 46, as will be described hereinafter. The cam 46 is mounted on the end of a shaft 48, which is rotated by means of a dial or knob 50. After passing through the variable orifice 44, the gas leaves the peak flow control valve 40 through an outlet 52, and is then conducted to the patients's air passage via the typical pneumatic components of the ventilator. It is advantageous to provide a bypass line 60, 62 to bypass the main circuit, (i.e., the waveform regulator, the solenoid valve, and the peak flow control valve) to provide the patient with a selected minimum flow rate regardless of the flow rate through the main circuit. The bypass line 60, 62 is controlled by a bypass valve 64 actuated by a solenoid 66, which is energized upon receipt of a signal from the breathing rate control circuitry.

In operation, the respiratory therapy practitioner selects a peak flow rate by adjusting the size of the orifice 44 in the peak flow control valve 40 by means of the knob 50. Upon receipt of a signal from the breathing rate control circuitry, the main valve solenoid 28 is actuated, opening the main valve 24. Gas from the breathing gas supply enters the waveform regulator 10 through the inlet 12. The waveform regulator regulates the pressure of the gas so that the pressure at the outlet 20 is a fixed increment, or pressure differential, above a reference pressure conveyed to the sensing port 16 by the line 18. In the embodiment illustrated in FIG. 1, this reference pressure is selected by a toggle valve 70, which functions as a pneumatic switch. The toggle valve 70 has an outlet 72 connected to the line 18, a first inlet 74, which is open to ambient atmospheric pressure, and a second inlet 76 which receives the pressure at the peak flow control valve outlet 52 from line 78. (The pressure at the valve outlet 52 is substantially the same as the patient's airway proximal pressure, the latter being slightly lower than the former due to a pressure drop induced by the system components downstream from the peak flow control valve 40. For purposes of this discussion, the valve outlet pressure may be considered the equivalent of patient proximal pressure, and will be denominated as such.)

A toggle handle 80 is movable between two positions indicated by schematic representations of a taper wave and square wave, respectively. The toggle handle 80 is connected to a toggle plate 82, so that when the former is moved to the taper wave position, the toggle plate closes the proximal pressure inlet 76 leaving the line 18 open to atmospheric pressure through the inlet 74 and the outlet 72. When the toggle handle is moved to the square wave position, the toggle plate 82 closes the atmospheric pressure inlet 74 so that the line 18 receives proximal pressure through the inlet 76 and the outlet 72. Thus, the operator, by moving the toggle handle 80 to the appropriate position, can select, as the reference pressure for the waveform regulator, either atmospheric pressure or patient airway proximal pressure.

If the taper wave mode is selected, the pressure at the regulator outlet 20 will be a fixed differential above a substantially constant reference pressure, i.e., atmospheric pressure. Since the main valve 24 is designed to effect a minimal pressure drop, gas entering the peak pressure control valve 40 will be at a substantially constant pressure. The outlet 52 of the peak pressure control valve, being in communication with the patient's air passages, receives the airway proximal pressure. At the beginning of the inhalation phase of the patient's respiratory cycle, the airway proximal pressure is at its minimum. Accordingly, at this point in the cycle, the pressure differential across the peak flow control valve is at its maximum, and flow to the patient will be at the peak flow rate. As the airway proximal pressure increases over the course of inhalation, the pressure at the outlet 52 increases so that the pressure gradient across the peak flow control valve decreases, resulting in a decaying or tapered rate of flow of gas to the patient through the peak pressure control valve. The amount of taper, i.e., the percent decrease in flow rate at the end of inhalation as compared with the peak flow rate, will depend on several factors, particularly the waveform regulator outlet pressure and the airway proximal pressure at the end of inhalation.

If square wave operation is selected, the waveform regulator will receive airway proximal pressure as the reference pressure in the sensing port 16. As the airway proximal pressure increases, the waveform regulator will adjust the pressure at the outlet 20 upwardly so as to maintain the aforementioned constant pressure differential between the outlet pressure and the reference pressure. Accordingly, the pressure received at the peak flow control valve 42 will be increased as the pressure sensed at the peak flow control valve outlet 52 increases, so that a constant pressure gradient is maintained across the peak flow control valve. Thus, the flow rate through the peak flow control valve will remain substantially constant throughout the inspiratory phase of the respiratory cycle, even as the airway proximal pressure is increasing.

As previously noted, in the embodiment shown in FIG. 1, the degree of taper depends largely upon the patient's proximal pressure at the end of inhalation and the regulator output pressure. The first factor will, of course, vary from patient to patient, and, even with the same patient, may vary from time to time, depending upon the patient's condition. The second factor, namely the regulator output pressure, will generally be substantially a constant during taper wave operations. Thus, it will be seen that for a particular patient, the taper wave setting will generally provide a substantially fixed amount of taper.

In certain circumstances, the practitioner may desire the option of varying the degree of taper for a given patient. The embodiment illustrated in FIG. 2 is designed to provide that option. This embodiment differs from the embodiment in FIG. 1 only in that the toggle valve 70 is replaced by a needle valve assembly 90. The needle valve assembly includes a relatively large diameter port 92, which can be opened to the ambient atmosphere to varying degrees by a needle valve 94. An inlet 96, having a restricted diameter orifice, receives the airway proximal pressure from the line 78. An outlet 98 communicates with the sensing port 16 of the waveform regulator via the line 18.

The operation of the FIG. 2 embodiment is as follows:

With the needle valve 94 closed, the peak flow control valve outlet pressure ("patient airway proximal pressure") is transmitted to the waveform regulator sensing port 16 from the line 78 via the restricted diameter inlet 96, the outlet 98 and the line 18. Thus, with the atmospheric pressure port 92 of the valve assembly 90 completely closed, the pressure at the waveform regulator outlet 20 increases at approximately the same rate as does the airway proximal pressure, thereby achieving normal square wave operation. Since the airway proximal pressure at any time after the initiation of inhalation is generally positive with respect to atmospheric pressure, air from the line 78 will flow through the inlet 96 and out of the atmospheric pressure port 92 as the latter is opened by means of the valve 94. The air flowing through the inlet 96 suffers a pressure drop due to the restricted diameter orifice of said inlet, this pressure drop being proportional to the flow rate through the inlet 96, which, in turn, is proportional to the size of the port 92 as determined by the valve 94. Thus, when the atmospheric port 92 is completely closed by the valve 94, there is no flow through the inlet 96, the pressure drop caused by the restricted inlet orifice is essentially zero, and the pressure at the outlet 98 is approximately airway proximal pressure as previously mentioned. As the valve 94 is gradually opened, the pressure drop experienced at the outlet 98 will be less than the airway proximal pressure in the line 78, and will increase more slowly than the airway proximal pressure. Thus, the pressure at the waveform regulator outlet 20 will likewise increase more slowly than the airway proximal pressure, so that there is a gradual drop in pressure at the peak flow control valve inlet 42, thereby resulting in a gradual decay in the flow rate from the peak flow control valve outlet 52. This more gradual flow rate decay can be termed a "partial taper", with the degree of taper being proportional to the degree to which the valve 94 is opened. With the valve 94 in its fully opened position, the flow rate through the inlet 96 will be sufficient to cause the pressure of the air flowing therethrough to drop almost to atmospheric pressure (assuming the area of the atmospheric port 92 is sufficiently large as compared to the area of the restricted orifice in the inlet 96). Thus, the pressure experienced at the outlet 98 will remain at, or very close to, atmospheric pressure regardless of the airway proximal pressure. This substantially atmospheric pressure is communicated, via the line 18, to the waveform regulator reference port 16, so that the maximum amount of taper, or "full taper", is achieved in the manner described above with reference to the embodiment of FIG. 1.

Thus, it can be seen that by manipulation of the valve 94, any desired degree of taper can be selected by the operator between square wave operation and full taper, for any peak flow rate setting of the peak flow control valve 40. Moreover, the embodiment of FIG. 2 offers the operator the option of maintaining the same degree of taper regardless of variations in peak airway proximal pressure due to changes in a particular patient's condition, or due to different pulmonary characteristics of different patients.

Figure 6:
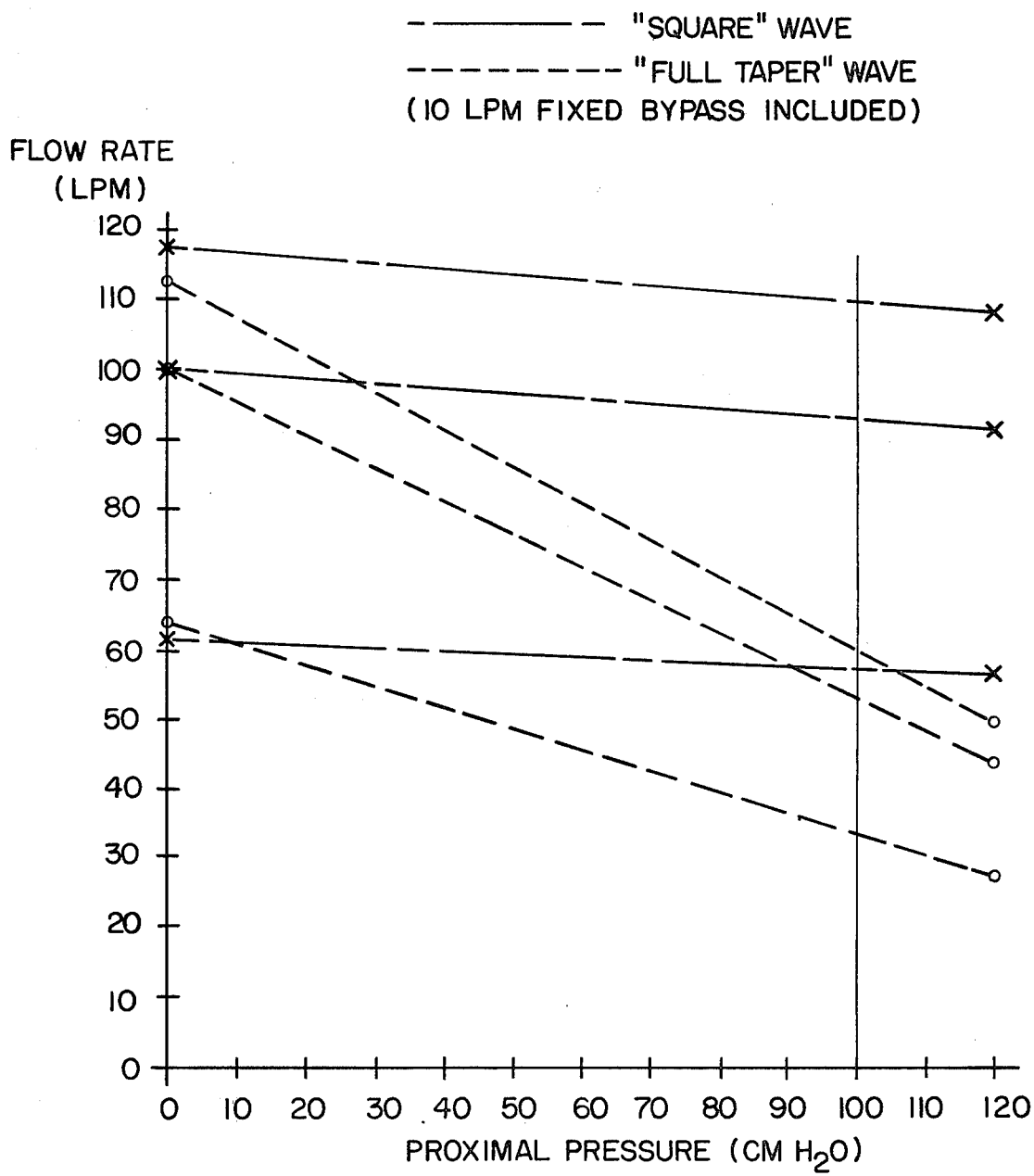
FIG. 6 is a graphical representation of the operation of the embodiment of FIG. 1.

FIG. 6 graphically illustrates the square wave and taper wave performance of the embodiment of the invention illustrated in FIG. 1. As illustrated in FIG. 6, square wave performance is represented by broken lines, and taper wave performance is represented by the dashed lines. As can be seen from the graph, "square wave" performance is not a perfect square wave; rather, for all values of peak flow rate (proximal pressure equals zero), there is approximately a 6% to 8% decrease in flow rate as proximal pressure rises to 100 centimeters of water (cm $H_2O$). This decrease in flow rate is largely due to the physical limitations of the components of the system, particularly the waveform regulator. Nevertheless, this performance compares very favorably with typical prior art systems which suffer up to a 20% decrease in flow rate over the same proximal pressure range. It will also be seen that the square wave performance is essentially constant throughout the range of peak flow rates from 60 to 120 LPM.

Viewing the taper wave performance, it can be seen that as proximal pressure rises to 100 cm $H_2O$, the flow rate decreases approximately 45% to 50%. Moreover, it can be seen that there is only a negligible difference in the peak flow rate between operation in the square wave mode and operation in the taper wave mode. (It should be noted that the curves using 100 LPM as the peak flow rate are calculated; the other curves were empirically derived. Also, all values were derived by including a constant 10 LPM bypass flow, and the proximal pressure values shown on the graph are actual patient airway proximal pressure, not the peak flow control valve outlet pressure, which would be slightly higher, as previously noted.)

It will be appreciated that with the embodiment of FIG. 2, the degree of taper can be varied continuously between 6% and 8% (square wave) and 45% to 50% (full taper wave).

FIG. 3 illustrates the modification made in the manostat described in U.S. Pat. No. 2,879,783 to Taplin, in order to adapt the device to suitable operation as the waveform regulator 10. Since the disclosure of the Taplin patent is incorporated herein by reference, it is necessary only to discuss the material modifications in the disclosed device.

As shown in FIG. 3, the reference port 16 of the regulator 10 communicates with a pressure sensitive aneroid capsule 102 via a passage 104 in a setscrew 106, which is attached to the top surface of the capsule 102. The setscrew 106 is used to adjust the pressure differential between the outlet pressure and the reference pressure, in a manner which will be understood by reference to the aforementioned Taplin patent. Access to the setscrew 106 is obtained by means of removal of a threaded plug 108 in the top of the regulator housing. Between the regulator inlet 12 and the regulator outlet 20, is a passage 110, having a valve seat 112 adapted to be engaged by a supply valve 114, which valve is constantly urged towards a closed position by a spring 116, supported in turn by a screw-threaded removable plug 118. The plug 118 is tapped to receive a screw 120, the shaft of which extends upwardly through the interior of the spring 116. A cylindrical projection 122 extends downwardly from the bottom of the valve 114, and when the valve 114 is opened, the projection 122 abuts against the shaft of the screw 120, thereby limiting the travel of the valve 114 as the valve opens. It has been found that by proper adjustment of the screw 120, the opening of the valve 114 can be controlled to minimize undesirable "spikes" in the flow rate waveform, which might otherwise occur at the beginning of the inspiratory part of the respiratory cycle, due to a pressure pulse resulting from the sudden opening of the valve 114 to its fullest extent without sufficient time for the regulator to respond. (It should be noted that the occurrence of such flow rate "spikes" is substantially eliminated by the placement of the waveform regulator 10 upstream from the main valve 24, as shown in FIGS. 1 and 2, since the pressure controlling elements of the regulator will then be pressure-charged with the pressure from the breathing gas supply before the main valve is opened. Accordingly, it may be found that modification of the Taplin device to incorporate the screw 120 may be unnecessary, except in those applications where the elimination of such waveform spikes is deemed critical, or where, for one reason or another, the waveform regulator is located downstream from the main valve.)

While the device described in the Taplin patent, modified as described above, is preferred for use as the waveform regulator, it should be understood that the waveform regulator function can be accomplished by any suitable pressure regulating device which is capable of providing an output pressure which has a fixed relationship with a reference pressure. Such a relationship may be expressed as:

$$P_o = P_r + \Delta P$$

where $P_o$ is the regulator output pressure, $P_r$ is the reference pressure, and $\Delta P$ is a fixed difference between $P_o$ and $P_r$.

Indeed, a pressure regulating device may be selected in which the relationship may be expressed as:

$$P_o = kP_r$$

where k is a positive constant. Such a device would increase the peak flow control valve inlet pressure, and, therefore, increase the pressure gradient across the peak flow control valve, to provide an increasing, or accelerating, flow rate as the airway proximal pressure increases (when the reference pressure is the airway proximal pressure.)

FIGS. 4 and 5 illustrate in detail the peak flow control valve 40, shown schematically in FIG. 1.

The peak flow control valve 40 comprises a body 402 having an interior valve chamber 404. Attached to the bottom of the body 402 is a cover plate 406, which is centrally apertured to provide the inlet 42. The inlet 42 extends into the interior of a hollow cylindrical boss 408, which projects inwardly from the cover plate 406 into the interior of the valve chamber 404. The boss 408 is apertured to provide a flow rate control orifice 410 communicating between the inlet 42 and the valve chamber 404.

The shaft 48 (shown schematically in FIG. 1) passes centrally through the valve body 402 and has an enlarged-diameter bearing portion 412, which engages the walls of a longitudinal bore 414. The bearing portion 412 may be circumferentially grooved to provide a seat 416 for a sealing o-ring 418. The bearing surface 412 of the shaft extends into the chamber 404 and terminates in a flat 420, which mates with a slot 422 in the valve cam 46 (shown schematically in FIG. 1). Extending from the flat 420 is a dowel pin 426, which extends through the center of the cam 46, terminating in a reduced diameter bearing 428, which is rotatingly mounted in the boss 408.

Carried between a circumferential flange 430 on the cam 46 and a thrust washer 432 seated at the opposite of the chamber 404 from the cam is a spring 434, which surrounds the shaft 48 and the cam 46 in the area of their juncture. The spring 434 urges the cam 46 against the surface of the boss 408 so as to provide a close engagement therebetween. As best shown in FIG. 4, the cam 46 is shaped so as to have a cam lobe 436 which, when the cam is rotated by means of the shaft 48, serves to close the orifice 410 to varying degrees, thereby varying the effective size of the orifice 410. The position of the cam lobe 436 with respect to the orifice 410 is varied by the rotation of the cam 46 via the shaft 48 and the knob 50. The smaller the effective size of the orifice 410, as determined by the location of the cam lobe 436, the lower the flow rate of gas will be through the orifice 410. The shape of the cam lobe 436 is specifically designed to achieve the desired peak flow setting calibration. Thus, the shape of the cam lobe 436 can be changed to meet particular calibration needs. To aid in selecting the proper setting of the peak flow rate adjustment orifice 410, the body 402 may carry a pair of posts 438 (one of which is shown in FIG. 5), which act as dial stops when engaged by a peg 440 radially extending from a disc 442 mounted on the shaft 48 external to the body 402. The posts 438 are advantageously located so as to correspond to the fully opened and fully closed settings of the orifice 410, and the disk 442 and the area of the body surrounding said disk may carry suitable indicia (not shown) to indicate various peak flow rate settings.

From the above, it can be seen that by turning the dial 50, the size of the peak flow adjustment orifice 410 can be increased or decreased to provide the desired peak flow rate from the inlet 42 to the outlet 52, which communicates with the chamber 404 through the body 402.

A bypass fitting 444 (FIG. 4) is advantageously provided on the body 402, said fitting having an inlet nipple 446, which receives the bypass line 62 (FIG. 1). The fitting 444 has an outlet 448, which opens into the chamber 404 downstream of the orifice 410, so that a suitable bypass flow is provided at all settings of the orifice 410, even when the latter is completely closed by the cam lobe 436.

In summary, it can be seen from the foregoing description that the disclosed invention provides several significant advances in the art of flow rate control in medical ventilators. Specifically, vastly improved square wave performance is achieved, while taper wave performance is given additional predictability and flexibility to accommodate a wide range of therapeutic needs. Furthermore, taper wave performance is achieved without any significant degradation in the peak flow rate, and without compromising square wave performance. Finally, the design of the peak flow control valve incorporated in the present invention allows precise peak flow rate settings, while also allowing flexibility in the calibration of such settings. The present invention thus provides the respiratory therapy practitioner with an heretofore unattainable degree of control of the ventilation procedure.

What is claimed is:

1. In a medical lung ventilator for delivering breathing gas to a patient at a controlled rate of flow, an improved gas flow rate control apparatus, comprising:
    first means for selecting a peak flow rate; and
    second means in fluid communication with said first means, for selectably (a) substantially maintaining the flow rate at least at said peak flow rate as said patient's airway proximal pressure increases and (b) allowing said flow rate to decay from said peak flow rate at a selected decay rate as said patient's airway proximal pressure increases.

2. The gas flow rate control apparatus of claim 1, further comprising:
    third means, communicating with said second means, for varying said selected decay rate.

3. The gas flow rate control apparatus of claim 1, wherein said first means includes a valve having an inlet, an outlet, an orifice between said inlet and outlet, and means for varying the size of said orifice, said inlet being in communication with said second means and said outlet being in communication with said patient's air passages.

4. The gas flow rate control apparatus of claim 3, wherein said second means selectably (a) increases the pressure at said inlet at least substantially at the rate that said patient's airway proximal pressure increases to maintain a substantially non-diminishing pressure gradient between said inlet and said outlet, and (b) maintains a substantially constant pressure at said inlet independently of changes in said patient's airway proximal pressure received at said outlet.

5. The gas flow rate control apparatus of claim 4, wherein said second means comprises:
    pressure sensing means for receiving a reference pressure;
    pressure regulating means for supplying a pressure at said inlet which is greater than said reference pressure by a known amount; and
    reference pressure selection means for selecting as said reference pressures either (a) a substantially constant pressure, or (b) a pressure which increases as said patient's airway proximal pressure increases.

6. The gas flow rate control apparatus of claim 5, wherein said substantially constant pressure is ambient atmospheric pressure, and said increasing pressure increases at substantially the same rate of increase as said patient's airway proximal pressure.

7. The gas flow rate control apparatus of claim 5, wherein said reference pressure selection means comprises:
    a first port communicating with said pressure sensing means;
    a second port communicating with said outlet of said first means and receiving therefrom a varying pressure having a fixed relationship with said patient's airway proximal pressure;
    a third port receiving said substantially constant pressure;
    valving means in said third port for selectably controlling the gas flow rate from said second port to said third port; and
    a restricted-diameter orifice in said third port for producing a pressure drop which is proportional to the gas flow rate from said second port to said third port, whereby said first port receives the pressure resulting from said pressure drop, said resulting pressure being substantially said varying pressure when said valving means completely closes said third port, and substantially said constant pressure when said valving means completely opens said third port.

8. A method of controlling the rate of flow of breathing gas delivered to a patient with a medical lung ventilator having a peak flow rate control valve, comprising the steps of:
    (1) Adjusting said valve to select a peak flow rate to said patient;
    (2) allowing the pressure at the outlet of said valve to increase as said patient's airway proximal pressure increases; and
    (3) selectably (a) maintaining a substantially constant pressure at the inlet of said valve to produce a decaying rate of flow as said patient's airway proximal pressure increases, and (b) increasing the pressure at said inlet at least at the rate of increase of said patient's airway proximal pressure to maintain a substantially non-diminishing pressure gradient across said valve, thereby maintaining a flow rate at least substantially at said peak flow rate.

9. In a medical ventilator having gas flow path means for delivering breathing gas to a patient at a controlled rate of flow, an improved gas flow rate control apparatus, comprising:
    first means, in said gas flow path means, for selecting a peak flow rate; and
    second means, in said gas flow path means, in fluid communication with said first means, and responsive to the pressure in said gas flow path means downstream from said first means, for selectably (a) substantially maintaining the flow rate at least at said peak flow rate as said patient's airway proximal pressure increases, and (b) allowing said flow rate to decay from said peak flow rate at a selected decay rate as said patient's airway proximal pressure increases.

* * * * *